United States Patent [19]

Marks

[11] Patent Number: 5,243,991
[45] Date of Patent: Sep. 14, 1993

[54] ADJUSTABLE BLOOD PRESSURE CUFF AND METHOD OF MEASURING BLOOD PRESSURE

[76] Inventor: Lloyd A. Marks, 727 Great Springs Rd., Bryn Mawr, Pa. 19010

[21] Appl. No.: 788,500

[22] Filed: Nov. 6, 1991

[51] Int. Cl.$^5$ ............................................. A61B 5/02
[52] U.S. Cl. ................................. 128/686; 128/680; 128/DIG. 15
[58] Field of Search .................... 128/774, 680–686, 128/898, 900, DIG. 15

[56] References Cited

U.S. PATENT DOCUMENTS

| | | |
|---|---|---|
| 1,970,042 | 8/1934 | Brathwaite . |
| 2,044,691 | 6/1936 | Hoflinger . |
| 3,442,270 | 5/1969 | Steinman . |
| 3,467,077 | 9/1969 | Cohen ................................. 128/686 |
| 3,570,495 | 3/1971 | Wright . |
| 3,765,405 | 10/1973 | Natkanski . |
| 4,066,084 | 1/1978 | Tillander . |
| 4,210,154 | 7/1980 | Klein . |
| 4,572,205 | 2/1986 | Sjonell . |
| 4,667,672 | 5/1987 | Romanowski . |
| 4,672,722 | 6/1987 | Malamed . |
| 4,716,906 | 1/1988 | Ruff . |
| 4,745,924 | 5/1988 | Ruff ................................. 128/686 |
| 4,901,732 | 2/1990 | Williams . |
| 4,926,848 | 5/1990 | Shimkus et al. . |
| 4,938,226 | 7/1990 | Danielsson et al. . |

Primary Examiner—Randall L. Green
Assistant Examiner—R. Clarke
Attorney, Agent, or Firm—Wigman, Cohen, Leitner & Myers

[57] ABSTRACT

A flexible blood pressure cuff for use in measuring the blood pressure of a patient, includes an inflatable bladder having a first side and a second side. One of the bladder sides is provided with hook and loop fasteners for adjustably and removably retaining at least a portion of one of the two bladder sides against a remaining portion of the one bladder side when the bladder is folded over itself. The effective inflatable width of the bladder is thereby adjusted to accommodate the circumference of the limb of the patient so that accurate blood pressure measurements may be obtained for each patient. According to the method, the blood pressure cuff is folded over itself to produce a cuff having an effective inflatable width which is adjusted according to the circumference of the limb of the patient whose blood pressure is to be measured.

19 Claims, 2 Drawing Sheets

ADJUSTABLE BLOOD PRESSURE CUFF AND METHOD OF MEASURING BLOOD PRESSURE

FIELD OF THE INVENTION

The present invention relates to an apparatus for and a method of measuring blood pressure and more particularly to an adjustable blood pressure cuff and method of using the cuff to measure blood pressure in proportion to the circumference of the limb where the measurement is taken.

DESCRIPTION OF THE PRIOR ART

A search of the prior art failed to reveal the adjustable blood pressure cuff or the method of measuring blood pressure according to the present invention. The following U.S. patents were uncovered which relate to blood pressure measurement or other medical devices: U.S. Pat. No. 3,570,495 to Wright; U.S. Pat. No. 4,210,154 to Klein; U.S. Pat. No. 4,572,205 to Sjönell; and U.S. Pat. No. 4,901,732 to Williams.

In particular, the patents to Williams, Klein and Sjonell are typical of the familiar blood pressure cuff which relies on the detection of Korotkoff sounds as the inflated cuff is deflated from above systolic pressure to below diastolic pressure. Other non-invasive techniques which employ an inflatable cuff include automated blood pressure devices which use the plethysmographic pulse transmitted from the inflated cuff or bladder; and the use of Doppler ultrasound. In the former technique, the cuff is deflated from suprasystolic pressures, the pulse amplitude appears at systolic pressure, reaches a maximum at or about mean pressure, and then decreases and disappears at diastolic pressure. In the latter technique, the sounds produced from movement of the blood pressure wall are absent when the cuff is inflated above systolic pressure and present at inflations below systolic pressure. It bears repeating that all of the above-described techniques use an inflatable cuff.

As noted in each of the Williams, Klein and Sjönell patents, critical diagnostic errors may arise because of the necessity to match the width of the cuff with the girth or circumference of the patient's limb to which the cuff is applied. For example, as noted in the Williams patent, the standard 12 centimeter width cuff is used in almost all instances, regardless of the build or size of the patient. Test have indicated that errors of 5-10 mm Hg or greater may exist in the measurement of both systolic and diastolic pressures, which may result in misdiagnosis. Klein further indicates that this problem is particularly acute in the case of measuring the blood pressure of children.

As Williams further notes, the American Heart Association recommends that a total of seven different cuff sizes be utilized to accommodate the range of patient arm widths, from pediatric to large adult size. Needless to say, this cumbersome procedure insures a lack of acceptance of the recommended seven different cuffs in the clinical setting.

To overcome the error resulting from an improper size cuff, it has been determined that the width of the inflatable part of the bladder overlying the artery should be approximately 40% of the circumference of the limb to properly occlude the artery during blood pressure measurement. In other words, the recommended cuff width is 0.4 times the arm circumference. To date, none of the proposed cuffs or blood pressure measurement methods have been sufficiently economical, practical and easily used so as to be widely accepted.

SUMMARY OF THE INVENTION

In view of the foregoing limitations and shortcomings of the prior art devices, as well as other disadvantages not specifically mentioned above, it should be apparent that there exists a need in the art for a blood pressure cuff which is adjustable for use on a variety of patients, regardless of the size of the limbs of the patient, as well as the age or other condition of the patient. It is also apparent that there is a need in the art for a method of measuring blood pressure in a more accurate and convenient fashion, and which is less costly and more efficient to put into practice.

It is, therefore, a primary object of this invention to fulfill that need by providing a single blood pressure cuff and method of measuring blood pressure using the cuff which will provide accurate diagnostic information for a wide spectrum of patients.

Another object of the invention is to provide a blood pressure cuff which is relatively simple in design and is thus readily manufactured.

It is another object of the invention to provide a blood pressure cuff which is of relatively simple construction so that it is easily used in practice.

It is yet another object of the present invention to provide a blood pressure cuff for which it is relatively easy to determine the appropriate cuff width as a function of the circumferential girth of the limb of the patient and to adjust the cuff width to make accurate blood pressure measurements in a convenient fashion.

Yet another object of the present invention is to provide a blood pressure cuff and a method of using the blood pressure cuff having the aforementioned accurate and convenient qualities so that the cuff and its method of use will gain wide acceptance in the medical field.

Briefly described, the aforementioned objects are accomplished according to the invention by providing a flexible, width-adjustable blood pressure cuff for use in measuring the blood pressure of a patient, the blood pressure cuff having an inflatable bladder having a first side and a second side. One side of the bladder is provided with a means or device for adjustably and removably retaining at least a portion of one of the two bladder sides against a remaining portion of the one bladder side when the bladder is folded onto itself. The effective inflatable width of the bladder is thereby adjusted in proportion to the actual circumference of the limb of the patient so that accurate blood pressure measurements may be obtained for each patient. An additional feature of the invention is the provision of an index line having a cuff width to limb circumference ratio of 0.4:1.

In its method aspects, the invention includes providing the blood pressure cuff having the features as described above. According to the method, the blood pressure cuff is folded over itself to produce a cuff having an effective inflatable width which is adjusted according to the circumference of the limb of the patient whose blood pressure is to be measured. The cuff is maintained in the proper folded condition by the retaining means disposed on the side of the cuff which is folded over itself. The cuff is then placed into position around the limb of the patient, inflated to the appropriate pressure, and then deflated while the blood pressure is measured. The index line provided on one side of the bladder may be used initially to determine the correct width to which the bladder should be folded to assure an accurate blood pressure measurement.

With the foregoing and other objects, advantages and features of the invention that will become hereinafter apparent, the nature of the invention may be more clearly understood by reference to the following detailed description of the invention, the appended claims and to the several views illustrated in the attached drawings.

DETAILED DESCRIPTION OF THE INVENTION

Figure 1:
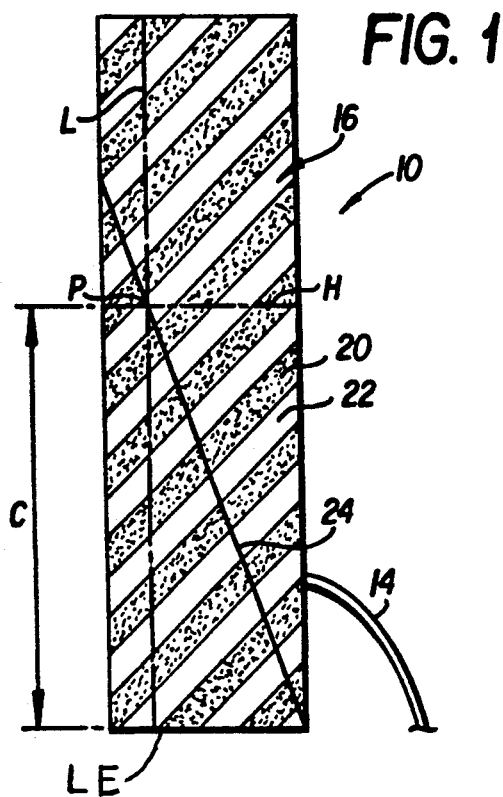
FIG. 1 is a top plan view of a blood pressure cuff in accordance with the present invention.

Referring now in detail to the drawings, wherein like numerals refer to the like parts throughout the various drawing figures, there is shown in FIGS. 1 through 5 a blood pressure cuff for use in the measurement of a patient's blood pressure in accordance with the invention, and designated generally by reference numeral 10. Blood pressure cuff 10, in the preferred embodiment, is generally rectangularly-shaped, having a width and length sufficient to extend about a limb of the greatest circumference to be measured and to overlap itself in the conventional manner. Blood pressure cuff 10 includes an elastomeric bladder 12 (FIG. 5) made of rubber or a synthetic elastomer which is inflatable by means of a tube 14 connected to a suitable inflation means (not shown), such as a conventional rubber bulb and valve, as is well known in the art.

Figure 2:
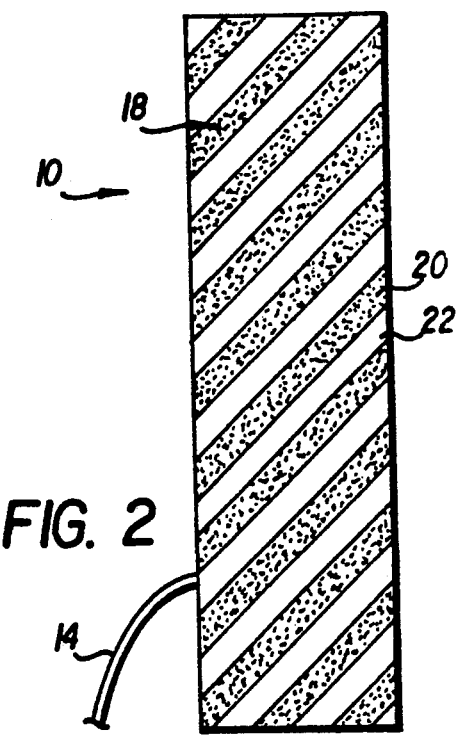
FIG. 2 is a bottom plan view of the blood pressure cuff of the invention.
Figure 3:
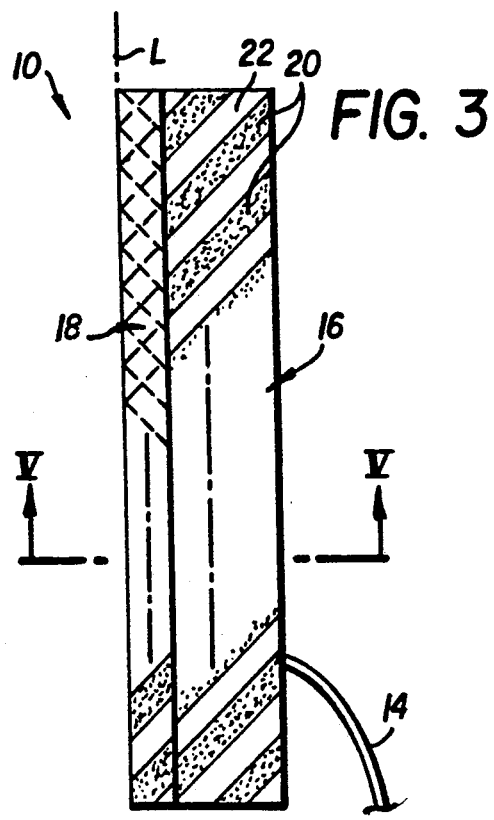
FIG. 3 is a top plan view of the blood pressure cuff of the invention, similar to FIG. 1, illustrating the manner in which the blood pressure cuff is folded over itself, in accordance with the invention.

Referring specifically to FIG. blood pressure cuff 10 is shown in its fully extended, unfolded condition, with a first surface 16 visible to the observer. Similarly, as illustrated in FIG. 2, blood pressure cuff 10 has a second surface 18 on the opposite side of the cuff 10. The first and second surfaces 16, 18 are covered with alternating hook fastener strips 20 and loop fastener strips 22, sold under the mark Velcro ®. Alternately, the surfaces 16, 18 may be covered with a fastener material of the types described in U.S. Pat. Nos. 4,672,722 to Malamed or 3,387,345 to Savoir.

In the preferred embodiment illustrated in FIGS. 1-5, strips 20,22 are each arranged at a 45° angle with respect to the edges of blood pressure cuff 10. In the illustrated embodiment, the strips 20,22 have a width of about ⅜ inch. Strips 20, 22 may be bonded to the exterior surface of bladder 12, such as by a suitable adhesive, or may be formed integrally with the bladder, or may be attached by suitable means to an enclosure or cover for the bladder, such as the fabric envelope used to cover the bladder of a conventional blood pressure cuff. As shown in FIG. 2, second surface 18 of the cuff 10 is also provided with a similar arrangement of alternating hook and loop fastener strips 20, 22 for a purpose which will be explained in detail hereinafter.

An additional important feature of the invention, as shown in FIG. 1, is the provision of a diagonal index line 24 on the first surface 16 of bladder 12. Index line 24 is a straight line having the slope $x = .4y$, where x is the width dimension and y is the longitudinal or length dimension. In terms of application to measurement of blood pressure, x, or the width dimension, represents the ideal width of the blood pressure cuff for a patient's limb having a circumference y.

With the foregoing in mind, and referring in particular to FIGS. 1 and 3-5, the operation of the inventive blood pressure cuff 10 will now be described in greater detail. First, the proper width of the cuff which will be used to take the blood pressure measurement of the individual patient is determined. This may be conveniently done by wrapping the unfolded cuff 10 about the limb of the patient with the first surface 16 facing the limb and noting the point at which the lower edge LE of the cuff intersects index line 24 (along horizontal axis H, at point P, in the case herein illustrated, for a limb having a circumference C). Alternatively, a flexible tape measure may be used to measure the circumference of the limb and the tape measure may then be used to determine point P with the cuff 10 laid flat in the form shown in FIG. 1 by measuring off the limb circumference C from the lower edge LE.

Figure 5:
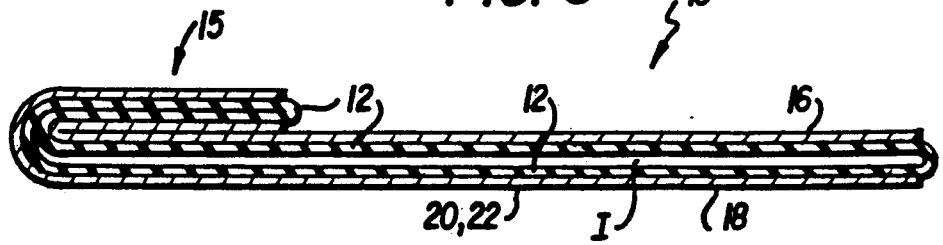
FIG. 5 is a cross-sectional view of the blood pressure cuff of the invention, taken along the line V—V of FIG. 3.

The blood pressure cuff 10 is then folded along a line parallel to the longitudinal axis of cuff 10, the fold line passing through intersecting point P of index line 24, or along longitudinal fold line L. Thus folded, blood pressure cuff 10 has the appearance illustrated in FIGS. 3 and 5 and has a width equal to the recommended 0.4 or 40% of the circumference of the limb on which the blood pressure is to be measured. In the folded condition, 50% of the material of loop strips 20 of first surface 16 which is folded against itself is in contact with 50% of the corresponding hook strips, to produce a secure yet removable fold retaining means for the adjustment of the width of the cuff 10. Further, as shown in FIG. 5, a folded over portion 15 is formed comprising four bladder layers and four hook-and-loop fastener layers in the area where the cuff is folded over itself. An inflation chamber I is disposed between the layers of the bladder 12 and has a width substantially the width of the folded cuff as shown in FIG. 5.

Figure 4:
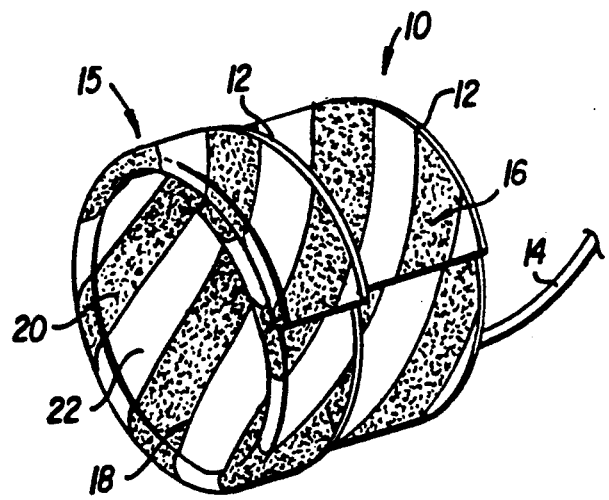
FIG. 4 is a perspective view of the blood pressure cuff of FIG. 3 showing the blood pressure cuff rolled to form a complete loop or toroid adapted for inflation so as to measure the blood pressure of the patient.

Once the cuff 10 has been folded to the appropriate width in proportion to limb circumference, the cuff is then ready to be wrapped around the limb of the patient. Preferably, a portion of the second surface 18 as shown in FIG. 5 is placed against or faces the limb of the patient and a portion of the first surface 16 together with the folded over portion 15 faces outwardly away from the limb of the patient. Alternately, the cuff may be inverted and applied with the folded portion confronting the limb of the patient. As shown in FIG. 4, the folded cuff 10 is then wrapped about the patient's limb and is fastened in place by contact between the hook-and-loop fasteners 20, 22 on the overlapping surfaces of the cuff. The mating of corresponding portions of hook and loop strips 20, 22 of each of surfaces 16, 18 produces fastening over approximately 50% of the mating surface area.

When the cuff 10 has been wrapped around the limb and secured in position as shown in FIG. 4, it is then inflated via tube 14 in a conventional manner. The inflatable chamber I within the bladder 12 is expanded across the folded cuff width which will provide accurate blood pressure measurements for the individual patient being examined. The cuff is then deflated and blood pressure is measured, either by listening for Korotkoff sounds, using automated blood pressure devices, doppler ultrasound techniques, or by any other appropriate non-invasive measurement technique.

As illustrated in the present embodiment, the index line 24 is a straight line and is positioned so that the folded width of the cuff is equal to a fixed, linear proportion of the limb circumference, namely, 40% or 0.4 of the limb circumference. However, it is contemplated that experimentation with the cuff of the present invention may show that the ratio of cuff width to limb circumference (W/C) is a function of limb circumference. For example, it may be found that the correct W/C for an arm having a 34 cm circumference is 0.38 and for an arm having a 38 cm circumference is 0.42. If so, the index line may be curved so that it provides an appropriate W/C correlation with a range of limb circumferences.

Further, the optimal W/C ratio may be determined to be different for different methods of blood pressure measurement, or for different materials or methods of construction. For example, measurement by Korotkoff sounds and measurement by automated devices or doppler based devices may require different W/C ratios. Accordingly, the index line could be modified to account for such differences as exist.

While the use of index line 24 for the measurement of the appropriate cuff width is an important feature of the present embodiment of the invention, it will be apparent that its provision and use is not an essential feature of the invention, and that measurement of the appropriate cuff width may be provided by other diverse means within the scope of the invention or may simply be calculated based on a tape measurement of limb circumference.

Further, while in the present illustrated embodiment of the invention, hook-and-loop strips have been provided over both the inside and outside surfaces of the cuff bladder, it will be appreciated that such strips, or other appropriate retaining means or devices may be provided on only one of either the inside or outside surfaces of the bladder in order to achieve the cuff width adjustment feature of the invention. It is within the scope of the present invention that conventional or other appropriate means may be provided for holding the bladder in place on the limb of the patient while blood pressure is being measured.

Figure 6A:
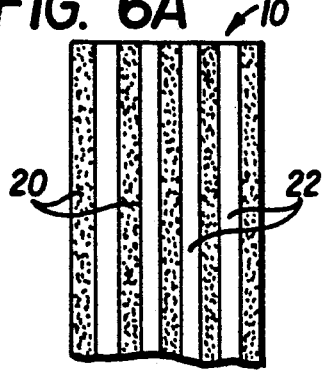
FIGS. 6A through 6F are partial plan views of either one or both sides of the blood pressure cuff of the invention, showing alternate embodiments thereof, in which various patterns of hook-and-loop fasteners are illustrated.
Figure 6B:
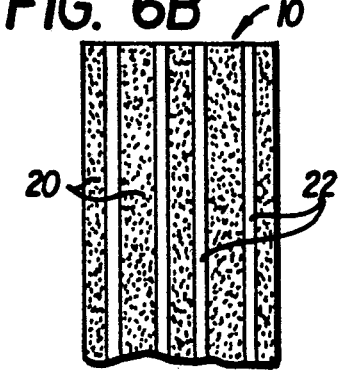
Figure 6C:
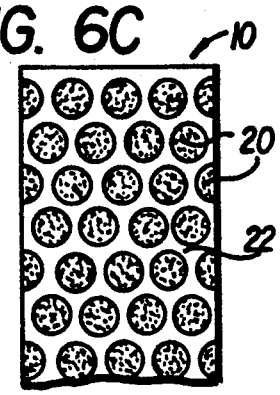
Figure 6D:
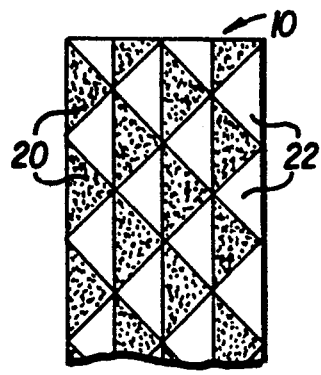
Figure 6E:
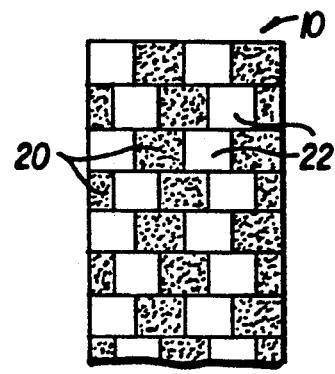
Figure 6F:
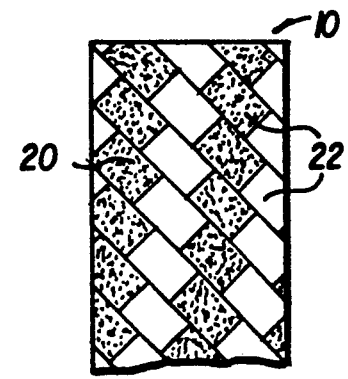

Referring now to FIGS. 6A through 6F, other additional embodiments of the invention are illustrated, in which variations in the pattern of hook and loop materials are seen. In FIG. 6A equal width, alternating hook and loop strips 20,22 run in a linear pattern parallel to the longitudinal axis of cuff 10. According to this arrangement, the intersection of hook area with loop area varies as a function of where the cuff is folded. In FIG. 6B alternating strips 20,22 are arranged similarly to FIG. 6A, but vary in width. According to this arrangement, there is no folded width dimension in which there is no intersection of hooks and loops. FIG. 6C illustrates a pattern in which geometric shaped pads of hook material, such as circular hooks, are surrounded by a field of loops, or vice versa. FIG. 6D illustrates a pattern in which the hooks and loops have the form of alternating triangles. FIG. 6E illustrates a pattern in which the hooks and loops are in the form of alternating, offset rectangles or squares. FIG. 6F illustrates a pattern in which the hooks and loops are in the form of alternating, offset diamond shapes or rectangles arranged along a diagonal to the cuff axis.

Figure 7:
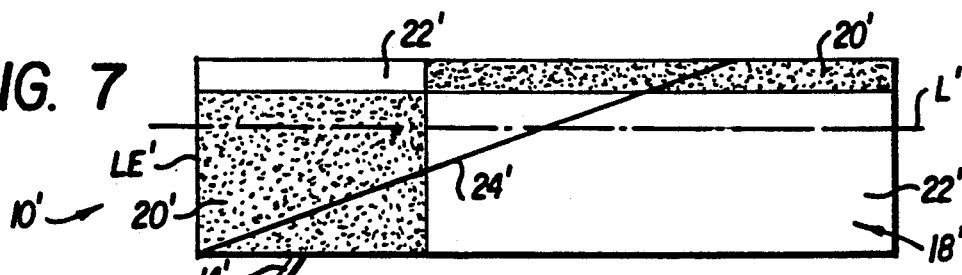
FIGS. 7-8 are top and bottom plan views, similar to FIGS. 1 and 2, of an additional embodiment of the invention.
Figure 8:
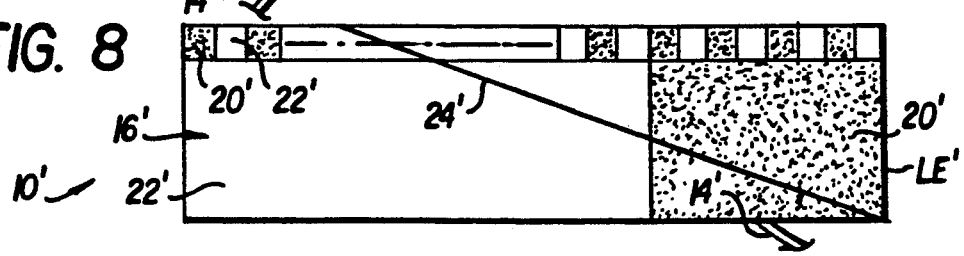

An additional embodiment of the invention is illustrated in FIGS. 7 and 8, in which the retention of the cuff in its folded position is accomplished by strategic positioning of the hook and loop material over the surfaces of the cuff. As illustrated in FIG. 7, blood pressure cuff 10' has front or outside surface 18' with strategically positioned hook material 20' and loop material 22'. Similarly, as illustrated as in FIG. 8, in which blood pressure cuff 10' has been turned over from the positions illustrated in FIG. 7 (note the positions of lower edge LE' and bladder tube 14'), hook material 20' and loop material 22' have been strategically positioned over back or inside surface 16' of cuff 10'. While the intersection of hooks and loops is not evenly distributed as in the embodiments heretofore illustrated and described, the functional requirements of holding the cuff along a selected fold and providing hook-and-loop intersections when the cuff is wrapped around the limb are both achieved. In this embodiment, index lines 24' are provided on both surfaces 16', 18' of the cuff 10'. A typical fold line L' is shown in FIG. 7.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

What is claimed is:

1. A foldable, adjustable blood pressure cuff having a length and a width and a longitudinal axis along the length thereof comprising a bladder having a first side and a second side, one of said sides being provided with means for adjustably and detachably retaining at least a portion of said one side in a folded condition against a remaining portion of said one side of said blood pressure cuff when said cuff is folded along an axis substantially parallel to its longitudinal axis, said retaining means comprising hook material and loop material affixed to said one of said sides such that when said cuff is folded into said folded condition said hook material engages said loop material.

2. The blood pressure cuff of claim 1, wherein said hook and loop material comprises alternating strips of hook and loop material.

3. The blood pressure cuff of claim 2, wherein the cuff is generally rectangular in shape and the strips of hook and loop material are disposed at an angle of about 45° with respect to the longitudinal axis of the cuff.

4. The blood pressure cuff of claim 3 in which the strips are disposed on said first side of said bladder.

5. The blood pressure cuff of claim 1, wherein said bladder includes means for removably retaining said cuff on a limb of a patient when said cuff is wrapped about said limb.

6. The blood pressure cuff of claim 5, wherein said means for removably retaining said cuff on said limb comprises hook and loop material.

7. The blood pressure cuff of claim 6, wherein said hook and loop material comprises alternating strips of hook and loop material disposed at an angle of about 45° with respect to a longitudinal axis of the cuff.

8. The blood pressure cuff of claim 1, wherein the hook and loop material comprises alternating hook and loop strips of equal width disposed parallel with respect to the longitudinal axes of the cuff.

9. The blood pressure cuff of claim 8, wherein the hook and loop material strips are of unequal width.

10. The blood pressure cuff of claim 1, wherein the hook and loop material comprises a series of hook material pads having a geometric shape and a field of loop material surrounding said geometric shapes.

11. The blood pressure cuff of claim 1, wherein the hook and loop material comprises a pattern of alternating triangles of hook and loop material.

12. The blood pressure cuff of claim 1, wherein the hook and loop material comprises a pattern in which the hook and loop material is strategically disposed over both of said side surfaces so as to hold the cuff along a selected fold line and provide hook and loop intersections when the cuff is wrapped around a limb of a patient.

13. A blood pressure cuff adapted to be wrapped about the limb of a patient for measurement of the patient's blood pressure, comprising:

a generally rectangularly-shaped bladder having a width and a length and a transverse axis along said width and a longitudinal axis along said length, the bladder further having an inside surface adapted to face the limb of the patient when the cuff is positioned around the limb of the patient for the blood pressure measurement, and having an outside surface adapted to face away from the limb of the patient when the cuff is positioned around the limb for blood pressure measurement;

said bladder being provided with hook material and with loop material on both the inside and the outside surfaces of said bladder, such that when the bladder is folded along a predetermined axis substantially parallel to said longitudinal axis through an angle of approximately 180°, the folded portion of said bladder is detachably secured to the other portion of said bladder by the hook material on one of said surfaces engaging the loop material on said one surface and when the bladder is wrapped about the limb of a patient, the hook material and loop material detachably secures the bladder about the limb of the patient.

14. A method of measuring blood pressure using a folding, adjustable blood pressure cuff comprising:

providing a bladder having a first side and a second side;

providing means associated with one of said first and second sides for adjustably and removably retaining at least a portion of one of said first and second sides in a folded condition against a remaining portion of said one of said first and second sides;

folding said blood pressure cuff such that a portion of one of said first and second sides is detachably retained against a remaining portion of one of said first and second sides;

placing said folded blood pressure cuff around the limb of a patient; and measuring the blood pressure in the limb of the patient.

15. The method of claim 14 further comprising:

providing means for removably retaining said first and second sides together when said sides are placed in contact with one another; and placing said sides in contact with one another to retain the cuff on the limb after placing the cuff around the limb of the patient.

16. The method of claim 14 further comprising:

providing a means for determining the appropriate width of the bladder to be inflated based on the circumference of the limb of the patient whose blood pressure is to be measured; and performing said folding step such that the folded width of the bladder to be inflated approximately equals the determined appropriate width of the bladder to be inflated based on the circumference of the limb of the patient whose blood pressure is to be measured.

17. The method of claim 16, wherein said means for determining the appropriate width of the bladder to be inflated is an index line provided on one of said first and second sides.

18. The method of claim 17, wherein the index line is a straight line having the slope $x=.4y$, where x is the width dimension of the cuff and y is the circumference of the limb of the patient.

19. The method of claim 17, wherein the index line is curved and fulfills an equation or a ratio correlating the cuff width to the circumference of the limb to be measured.

* * * * *